Feb. 25, 1941. L. B. CODDINGTON Plant Pat. 452
ROSE PLANT
Filed Oct. 5, 1940
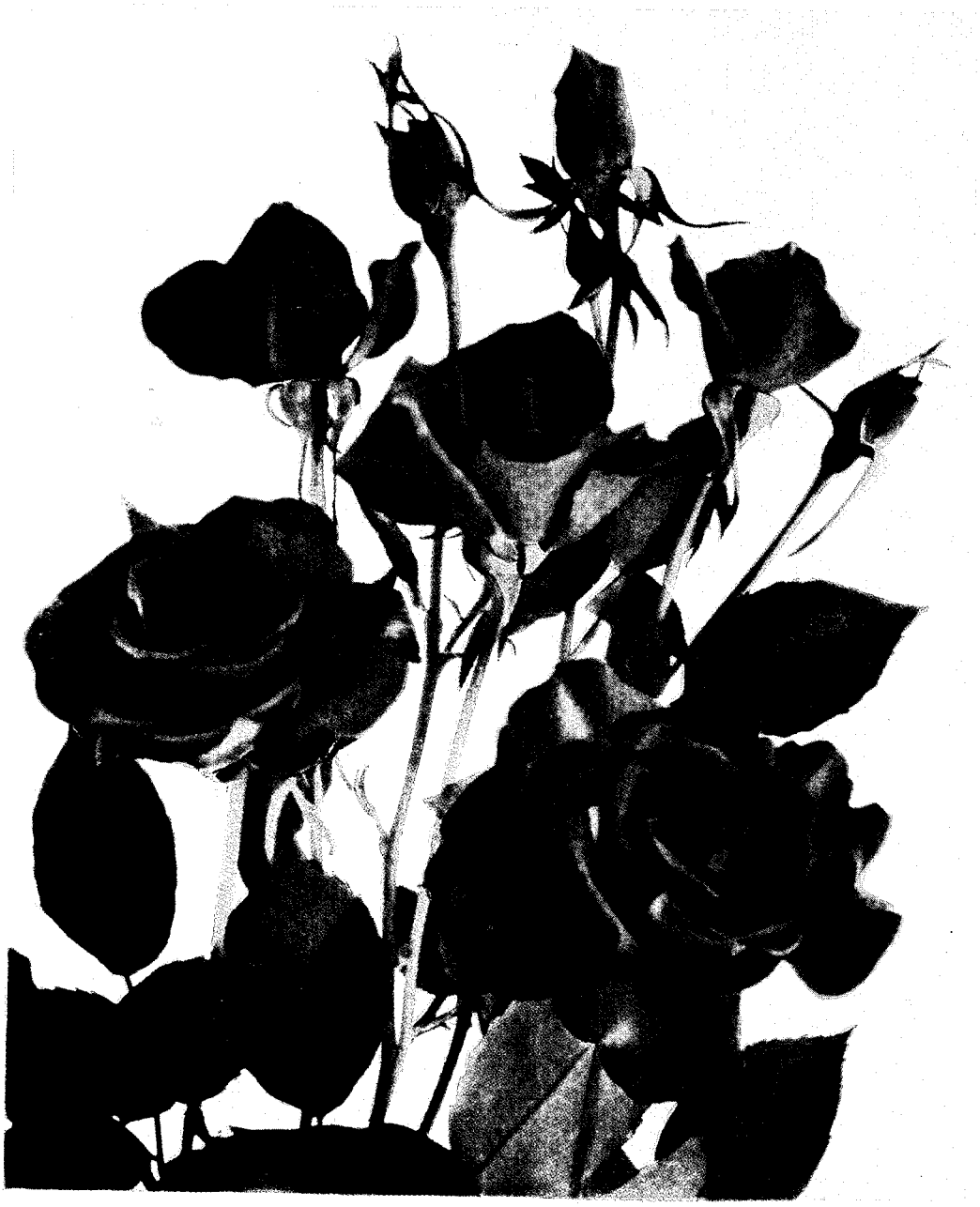
Inventor
L. B. Coddington
By Robb & Robb
Attorneys Patented Feb. 25, 1941

Plant Pat. 452

UNITED STATES PATENT OFFICE

452

ROSE PLANT

Lyman B. Coddington, Murray Hill, N. J., assignor to L. B. Coddington Co., Murray Hill, N. J., a corporation of New Jersey Application October 5, 1940, Serial No. 359,955

1 Claim. (Cl. 47—61)

The present discovery relates to a new and distinct variety of hybrid tea rose plant, originating as a sport of the well known variety "Better Times" (Plant Patent #23).

This new rose is characterized as to novelty primarily by its decided difference from the parent as shown in the color of the bloom, more specifically set forth hereinafter; its greater fragrance; the attractive velvety appearance of the blooms, and the persistence with which the blooms retain their true color over a period of several days.

In addition to the foregoing, one of the important points of distinction of this new variety lies in the character of foliage which is more specifically referred to hereinafter under the suitable heading for this feature of the plant.

In other respects, the new rose possesses (like its parent) definite features of particular value which render it especially desirable as a cut flower.

The following is a detailed description of the new variety, the color terms employed being general dictionary terms, except where otherwise specifically noted in relation to Ridgway's Color Standard by plate designations:

Type: Half hardy; greenhouse; sport; for cut flowers.
Class: Hybrid tea.
Breeding or discovery:
*Sport*: Parent—Better Times.
*Propagation:* Holds its distinguishing characteristics through succeeding propagations by cuttings, grafting, and budding.

*Flower*

Locality where grown: Murray Hill, New Jersey.
Flowers borne: Singly in regular cluster on strong long stems.
Quantity of bloom: Free in greenhouse.
Continuity: Continuous.
Fragrance: Strong; spicy.
Bud:
*Peduncle.* — Long; medium heavy; stiff; green; almost smooth; few green thorns.
*Before calyx breaks.—Size*—medium. *Form*—Long, pointed without foliaceous appendages on the surface of the bud; with slender foliaceous parts extending beyond the tip of the bud equal to one-half of its length.

*As calyx breaks.—Color*—Red.
*As first petal opens.—Size*—medium. *Form*—pointed. *Color:* Outside—Satiny Red; Inside — Dark velvety red. *Opening* — Opens up well—controlled by greenhouse temperature.

Bloom:
*Size, when fully open.*—Large, 5¼ to 5$\frac{11}{16}$ inches.
*Petalage.*—Double; from 24 to 27 petals, arranged regularly.
*Form.*—High center at first, becoming high centered; petals remaining at first tightly cupped inward; becoming later, at maturity, loosely cupped inward.
Petals: Thick, with inside velvety and outside satiny.
*Shape.* — Outside — ovate; intermediate — ovate; inside—ovate.
This description of a newly opened flower was made from a rose grown in a greenhouse, in June, 1940, at Murray Hill, New Jersey.
*Color.*—Face of petals—velvety texture, tones of Carmine Spectrum Red, Plate I; Rose Red, Plate XII; shaded with Maroon, Plate I. Back of petals—Satin texture, tones of Oxblood Red, Plate I, Van Dyke Red, Plate XIII.
This description was made from a rose that was open for three days in a greenhouse, in June, 1940:
*Color.*—Face of petals—velvety texture, tones of Carmine, Spectrum Red, Plate I; Rose Red, Plate XII; shaded with Maroon, Plate I. Back of petals—satin texture, tones of Oxblood Red, Plate I, Van Dyke Red, Plate XIII.
*General color effect.*—Newly opened flower—beautiful Dark Velvet. Three days open—color remains true.
*Behavior.*—Drop off cleanly—grown in greenhouse.
*Flower longevity.*—Cut roses grown in greenhouse in June have kept in refrigerator twelve days, retaining good color.

*Reproductive organs*

Stamens: Medium number arranged regularly about pistils tucked in calyx.
Filaments: Medium length; reddish; with anthers.
Anthers: Medium size; brown; open at various times.
Pollen: Moderate; yellow.
Pistils: Few.
Styles: Uneven; short; medium heavy; loosely separated.
Stigma: White.
Ovaries: All enclosed in calyx.
Hips: Short with inconspicuous neck: green; smooth; walls thin.
Sepals: Permanent; moderate length; straight.
Seeds: Few; small.

*Plant*

Foliage:

*Leaves.*—Compound of five; normal; medium size; leathery.

*Leaflets.*—Ovoid; base round; margin serrate.

*Color.*—Face—Dark Dull Yellow Green, Plate XXXII, Yew Green, Plate XXXI; serrated edge—near Burnt Umber, Plate XXVIII; mid rib—Vinaceous Russet, Plate XXVIII, blending to petiole of Etruscan Red, Plate XXVII; back—Deep Grape Green, Plate XLI, flushed with Army Brown, Plate XL, edge—Burnt Umber, Plate XXVIII.

*Rachis* (the supporting stem of the compound leaf).—Medium heavy. Upper side and under side—smooth.

*Stipules.*—Medium length; medium width, with moderately short points, turning out at an angle of 90°, recurved toward the stem.

By way of summary, one of the important marks of distinction of this variety is found in the foliage of the rose which, when young, is a reddish bronze, using general color terminology, which also is the color characteristic of the young wood. When the foliage matures, it is a dark green, as indicated in the above description, having a slight bronze cast, and this characteristic of growth makes this rose outstanding.

Growth:

*Habit.*—Upright.

*Growth.*—Vigorous.

*Canes.*—Medium heavy.

*Main stems.*—Near flower—Calliste Green, Plate VI; larger stems—Parrot Green, Plate VI, Cedar Green, Plate VI. *Thorns*—few; medium length; straight downward; with narrow base. *Prickles*—none. *Hairs*—none. *Branches*—green. *Thorns*—few; medium length; straight; with narrow base. *Prickles*—none. *Hairs*—none.

*New shoots.*—Red. *Thorns*—few; medium length; straight; hooked downward, with narrow base. *Color*—Etruscan Red, Plate XXVII. *Prickles*—none. *Hairs*—none.

I claim:

A new and distinct variety of hybrid tea rose plant, characterized as to novelty by the decided difference between it and its parent as regards the color of its bloom, its greater fragrance, the persistence of the color without change over a long period of time, and the color characteristics of the foliage, which, when young, is a reddish bronze as is also the young wood, and which, when mature, is a dark green having a slight bronze cast, substantially as shown and described.

LYMAN B. CODDINGTON.